US008673210B2

(12) United States Patent  
Deshays

(10) Patent No.: US 8,673,210 B2
(45) Date of Patent: Mar. 18, 2014

(54) METHOD FOR TRACKING THE USE OF A MEDICAL APPARATUS

(75) Inventor: Clement Deshays, Ruoms (FR)

(73) Assignee: Germitec, Clichy (FR)

(*) Notice: Subject to any disclaimer, the term of this patent is extended or adjusted under 35 U.S.C. 154(b) by 947 days.

(21) Appl. No.: 12/594,160

(22) PCT Filed: Apr. 3, 2008

(86) PCT No.: PCT/FR2008/000464
§ 371 (c)(1),
(2), (4) Date: Nov. 5, 2009

(87) PCT Pub. No.: WO2009/004126
PCT Pub. Date: Jan. 8, 2009

(65) Prior Publication Data
US 2010/0145721 A1 Jun. 10, 2010

(30) Foreign Application Priority Data
Apr. 5, 2007 (FR) .................. 07 54299

(51) Int. Cl.
A61L 2/00 (2006.01)
G01D 11/26 (2006.01)
B08B 7/00 (2006.01)
G08B 7/04 (2006.01)
G08B 9/00 (2006.01)

(52) U.S. Cl.
USPC .......... 422/3; 422/1; 422/22; 422/26; 422/28; 422/119; 134/6; 134/18; 134/22.1

(58) Field of Classification Search
USPC ............ 422/1, 3, 22, 26, 28, 119, 292, 300; 134/6, 18, 22.1
See application file for complete search history.

(56) References Cited

U.S. PATENT DOCUMENTS 4,772,795 A    9/1988   Sakurai et al.
4,948,566 A    8/1990   Gabele et al.
5,185,532 A    2/1993   Zabsky et al.
(Continued)

FOREIGN PATENT DOCUMENTS

DE    32 09 701 A1    9/1983
DE    39 17 876 A1    12/1990
(Continued)

OTHER PUBLICATIONS

International Search Report for PCT/FR2008/000464, mailing date Feb. 23, 2009.

(Continued)

Primary Examiner — Monzer R Chorbaji
(74) Attorney, Agent, or Firm — Morrison & Foerster LLP

(57) ABSTRACT

The method of the invention comprises the following steps: during the disinfection (A) of the apparatus, recording (1) with an acquisition and processing system the disinfection date and data relative to the apparatus disinfection type and level together with identification information of said apparatus; during the use (C) of the apparatus on a patient, recording (5) with said system the date and information concerning the apparatus type of use and the patient together with identification information of said apparatus; sequencing with the acquisition and processing system the information on the disinfection and use on a patient together with identification information of said apparatus; before each use, developing using the acquisition and processing system an instruction allowing or forbidding (6) the use of the apparatus based on the sequencing.

18 Claims, 2 Drawing Sheets

(56) References Cited

U.S. PATENT DOCUMENTS

Figure 1:
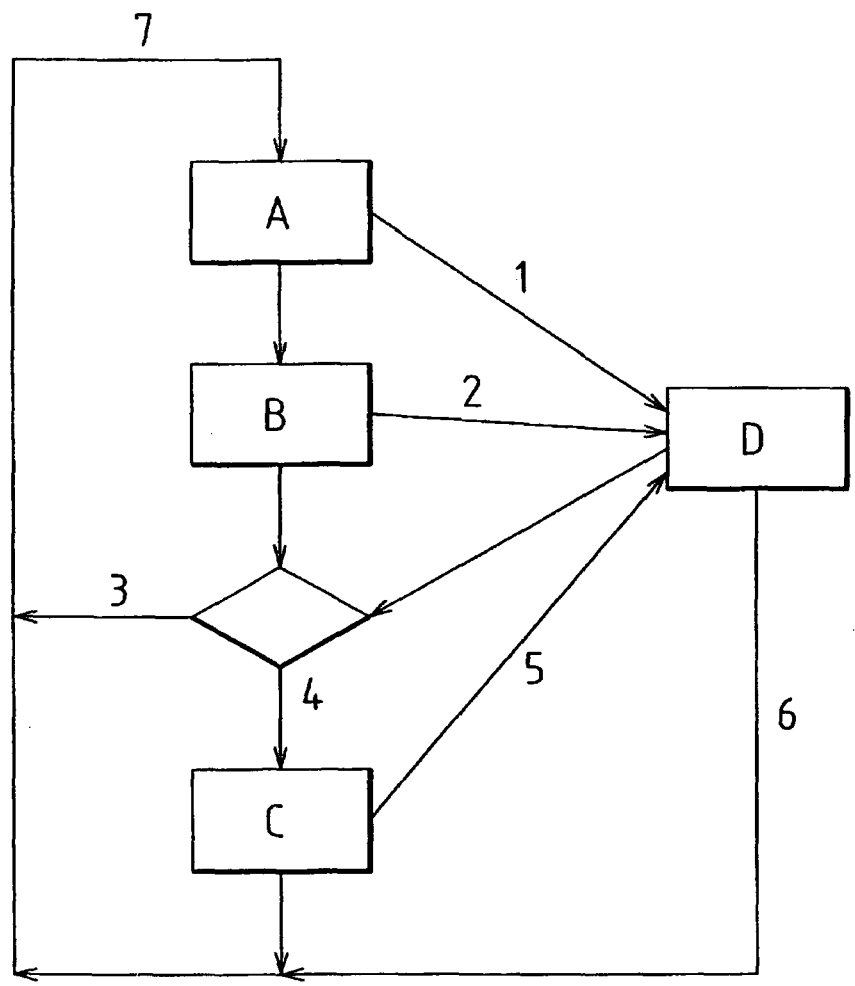

| | | |
|---|---|---|
| 5,310,524 A | 5/1994 | Campbell et al. |
| 5,610,811 A | 3/1997 | Honda |
| 5,641,464 A | 6/1997 | Briggs, III et al. |
| 5,690,113 A | 11/1997 | Sliwa, Jr. et al. |
| 5,761,069 A | 6/1998 | Weber et al. |
| 5,912,818 A | 6/1999 | McGrady et al. |
| 6,039,928 A | 3/2000 | Roberts et al. |
| 6,171,559 B1 | 1/2001 | Sanders et al. |
| 6,231,819 B1 | 5/2001 | Morello |
| 6,260,560 B1 | 7/2001 | Walta |
| 6,371,326 B1 | 4/2002 | Gabele et al. |
| 6,475,433 B2 | 11/2002 | McGeorge et al. |
| 6,485,979 B1 | 11/2002 | Kippenhan et al. |
| 6,641,781 B2 | 11/2003 | Walta |
| 6,712,756 B1 | 3/2004 | Kura et al. |
| 7,694,814 B1 | 4/2010 | Cristobal et al. |
| 7,965,185 B2 | 6/2011 | Cambre et al. |
| 7,982,199 B2 | 7/2011 | Deshays |
| 8,313,017 B2 | 11/2012 | Deshays |
| 8,334,521 B2 | 12/2012 | Deshays |
| 2001/0024623 A1 | 9/2001 | Grimm et al. |
| 2002/0161460 A1 | 10/2002 | Noguchi |
| 2002/0162972 A1 | 11/2002 | Pleet |
| 2003/0016122 A1 | 1/2003 | Petrick |
| 2003/0039579 A1 | 2/2003 | Lambert et al. |
| 2003/0091471 A1 | 5/2003 | Lacabanne |
| 2003/0187586 A1 | 10/2003 | Katzenmaier et al. |
| 2004/0009091 A1 | 1/2004 | Deal et al. |
| 2004/0140347 A1 | 7/2004 | Mihaylov et al. |
| 2004/0209223 A1 | 10/2004 | Beier et al. |
| 2005/0196314 A1 | 9/2005 | Petersen et al. |
| 2007/0027459 A1 | 2/2007 | Horvath et al. |
| 2008/0213139 A1 | 9/2008 | Deshays |
| 2009/0065034 A1 | 3/2009 | Suzuki et al. |
| 2009/0169436 A1 | 7/2009 | Deshays |
| 2010/0138234 A1 | 6/2010 | Deshays |
| 2010/0140342 A1 | 6/2010 | Deshays |
| 2010/0145721 A1 | 6/2010 | Deshays |

FOREIGN PATENT DOCUMENTS

| | | |
|---|---|---|
| DE | 4420707 A1 | 12/1994 |
| DE | 19514284 A1 | 10/1996 |
| DE | 197 03 823 C1 | 5/1998 |
| DE | 199 17 206 A1 | 10/2000 |
| DE | 102 25 232 A1 | 12/2002 |
| DE | 102 25 857 A1 | 1/2004 |
| EP | 0 471 530 A1 | 2/1992 |
| EP | 0 630 820 A1 | 12/1994 |
| EP | 0 709 056 A1 | 5/1996 |
| EP | 0 709 056 B1 | 5/1996 |
| EP | 0 839 537 A1 | 5/1998 |
| EP | 1155654 A1 | 11/2001 |
| EP | 1402904 A1 | 3/2004 |
| EP | 1 532 989 A1 | 5/2005 |
| FR | 2 753 905 A1 | 4/1998 |
| FR | 2 890 566 A1 | 3/2007 |
| FR | 2 890 864 A1 | 3/2007 |
| FR | 2 890 865 A1 | 3/2007 |
| WO | WO-84/00009 A | 1/1984 |
| WO | WO-99/08137 A1 | 2/1999 |
| WO | 99/66444 A1 | 12/1999 |
| WO | WO-01/80908 A1 | 11/2001 |
| WO | WO-2004/111917 A1 | 12/2004 |
| WO | 2005/048041 A2 | 5/2005 |
| WO | WO 2005/048041 A1 * | 5/2005 |
| WO | WO-2006/115177 A1 | 11/2006 |
| WO | WO-2007/016101 A1 | 2/2007 |
| WO | WO-2007/034083 A1 | 3/2007 |

OTHER PUBLICATIONS

International Search Report mailed on Feb. 23, 2009 for PCT Application No. PCT/FR2008/000465, filed on Apr. 3, 2008, 3 pages.

International Search Report mailed on Jan. 22, 2009, for PCT Application No. PCT/FR2008/000540, 3 pages.

International Search Report mailed on Jan. 22, 2009, for PCT Application No. PCT/FR2008/000541, 3 pages.

International Search Report mailed on Sep. 11, 2007, for PCT Application No. PCT/FR2007/000594, 3 pages.

International Search Report mailed on Jul. 18, 2006, for PCT Application No. PCT/FR2005/003034, 3 pages.

International Search Report mailed on Jul. 6, 2006, for PCT Application No. PCT/FR2005/003032, 3 pages.

International Search Report mailed on Mar. 21, 2006, for PCT Application No. PCT/FR2005/003031, 3 pages.

* cited by examiner

METHOD FOR TRACKING THE USE OF A MEDICAL APPARATUS

The present invention relates to a method for tracking the use of a probe-type medical apparatus in order to determine whether this apparatus may be safely used from a hygienic standpoint, as well as a tracking system that makes it possible to implement this method.

In the medical field, sanitation of the medical apparatuses being used is crucial in order to avoid any risk of infecting a patient because of an apparatus that has been poorly disinfected or not disinfected. For this reason, it is essential to ensure traceability of the disinfection process in order to be certain that an apparatus has in fact been disinfected before it is used.

Currently, this traceability is provided through manual operations by medical personnel. That is, the medical probe is accompanied by a record on which medical personnel must write the disinfection operations that have been carried out, along with the way the probe is used. In some cases, traceability is partially automated, and the information about a probe is assembled in a database. However, in this latter case, medical personnel must still enter the information regarding probe disinfection and use into the database themselves. Consequently, traceability is based on many human actions that can be sources of errors and/or falsification. Therefore, it is impossible to be absolutely certain whether a probe may be legitimately used from the standpoint of hygiene and of preventing nosocomial infections.

The purpose of the invention is to remedy these disadvantages by proposing a method for tracking the use of a probe in which the process of determining the legitimacy of using the probe is automated, and human involvement is limited.

To this end, an object of the invention is a method for tracking the use of a probe-type medical apparatus in order to determine whether this apparatus can be safely used from a hygienic standpoint, wherein said apparatus comprises means for identifying said apparatus and the method uses an information acquisition and processing system comprising means for acquiring information identifying said apparatus, means for acquiring information regarding the disinfection and use of said apparatus, and means for associating the identification and use information for said apparatus, the method comprising the following stages:

when the apparatus is disinfected, the acquisition and processing system records the date of disinfection and the disinfection information regarding the type and degree of disinfection of the apparatus, in conjunction with the identification information for said apparatus, when the apparatus is used on a patient, the acquisition and processing system records the date and information on use regarding the type of use of the apparatus and regarding the patient, in conjunction with the identification information for said apparatus, the acquisition and processing system sequences the disinfection information and the information regarding use on a patient in conjunction with the identification information for the apparatus, prior to each use, the acquisition and processing system produces an order authorizing or prohibiting the use of the apparatus based on the sequencing, with its use being authorized if, following a particular use, an appropriate disinfection process for this use has taken place, and its use being prohibited otherwise.

"Sequencing" is taken to mean that the information on disinfection and the information on use are put in order according to the moment in time when they were recorded, so as to create an event history for the medical apparatus.

The invention thus makes it possible to prohibit the use of the medical apparatus if using it is not legitimate from the standpoint of hygiene, e.g., if the apparatus has not been adequately disinfected or if too much time has elapsed since the apparatus was disinfected. This way, effective traceability is provided for the medical apparatus, which has no chance of being used if a certain chain of events (the disinfection stage) has not first taken place.

According to other characteristics of the method:

it additionally comprises a stage in which information regarding the apparatus storage time is recorded by the acquisition and processing system, wherein said storage information is sequenced in with the disinfection and use information, and the acquisition and processing system produces a disinfection order if the storage time exceeds a predetermined threshold and an order prohibiting the use of the apparatus if this disinfection has not taken place, recording the information about the type and degree of disinfection includes recording the active principle used for disinfection, the length of time the apparatus was exposed to this active principle, the disinfection temperature and/or the active principle dosage, the acquisition and processing system produces a notice of adequate or inadequate disinfection, based on the information about the type and degree of disinfection, and if the notice of inadequate disinfection is issued, the system produces an order prohibiting the use of the apparatus, during disinfection of the apparatus, the identity of the operator performing the disinfection is recorded, recording the information regarding the type of use of the apparatus includes recording the identity of the attending physician, the identity of the patient, the type of treatment for which the apparatus is used, the type of pathology of the patient, the length of time the apparatus is used, the information on the environment in which the apparatus is used and/or information on the system in which the apparatus is used, the acquisition and processing system records a history tracking the use of the medical apparatus and the legitimacy of its use.

The invention also relates to a system for tracking the use of a probe-type medical apparatus that makes it possible to implement the method as described above, said system being characterized in that it comprises identification means associated with the medical apparatus, an information acquisition and processing system comprising means for acquiring the information identifying said apparatus, means for acquiring information regarding the use of said apparatus, date and time recording means, and means for associating identification and use information for said apparatus with date and time information.

According to other characteristics of the system:

the means for acquiring the identification information, the means for acquiring use information regarding the use of said apparatus, and the date and time recording means are assembled in an independent, portable device able to communicate with an information processing system, the identification means associated with the medical apparatus comprise an RFID chip permanently fixed on said apparatus, the means for acquiring the medical apparatus identification information from the acquisition and processing system comprise means for remotely scanning an RFID chip, it comprises means for measuring the degree of disinfection provided by a disinfection enclosure, it comprises means for inputting information regarding the use of the medical apparatus, it comprises means for storing information acquired and processed by the acquisition and processing system.

Figure 2:
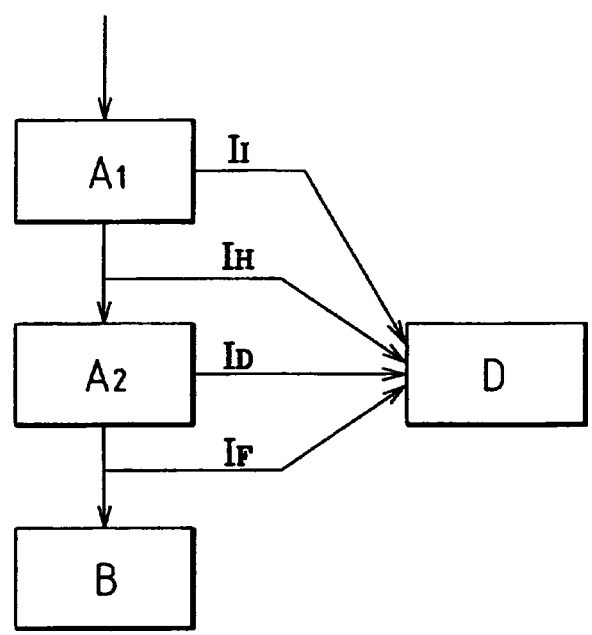

The invention will be more easily understood in the following description, given only as an example, and written with reference to the annexed drawing, in which:

FIG. 1 is a diagram representing the various stages of the tracking method according to the invention, FIG. 2 is a diagram detailing the disinfection stage of the method.

The medical apparatus according to the invention is, for example, a probe used with an ultrasonograph in a known manner. Such a probe will not be described in detail here, but typically comprises an active part and a part that connects to the ultrasonograph. The active part, which is in contact with the patients during a medical exam, must be sterilized without fail before being used on a patient in order to ensure satisfactory hygiene and prevent nocosomial infections.

Thus, it is mandatory to be able to trace probe disinfection and use in order to determine whether the active part of the probe has in fact been adequately disinfected before the probe is used on a patient. In order to provide this traceability, the probe comprises identification means permanently fixed on the probe.

These identification means are specific to each probe. In order to enable the tracking system to be automated, these identification means comprise an RFID chip molded into a plastic housing fixed to the probe or embedded in the material that forms the probe, for example. These identification means may be scanned remotely by means for acquiring the probe identification information.

The acquisition means comprise an RFID reader, for example, able to scan the information contained on the RFID chip associated with the probe. The identification information can be transmitted to a central data processing unit D that is part of a data acquisition and processing system that makes it possible to track the use of the probe, as will be described below.

During a stage A shown in FIG. 1, the probe is disinfected. Prior to being disinfected, the probe is identified and the date of disinfection is recorded, along with the time disinfection begins (stage A1 in FIG. 2). When disinfection is finished, the disinfection ending time is recorded. The identification information $I_i$, the date and exam starting time $I_h$ information, and the disinfection ending time information $I_f$ are transmitted to the central data processing unit D, as shown by the arrow 1 in FIG. 1 and by FIG. 2. A record is also made of the identity of the operator performing disinfection.

The means for acquiring the identification information and the date and time recording means can be associated with a disinfection enclosure or can be part of an independent, portable device placed in the disinfection room.

According to an embodiment, the independent, portable device is attached to the probe so that it follows the probe wherever it goes. An independent device of this kind can be an electronic label, for example, associated with a memory and attached to the probe.

According to an embodiment, the disinfection enclosure is provided with identification means so that the identity of the enclosure used for disinfecting the probe is transmitted to the data processing unit D.

Disinfection is performed during a stage A2. For example, disinfection is performed by exposing the active part of the probe to UV radiation, by soaking it in a bath comprising an active principle for disinfection, by exposing it to a liquid spray or by exposing it to a gas comprising an active principle for disinfection. In any case, means for acquiring information regarding the use of said apparatus make it possible to record the disinfection characteristics. These acquisition means comprise, for example, means for measuring the degree of disinfection provided by a disinfection enclosure. The recorded information can include a record of the active principle used for disinfection, the length of time the apparatus was exposed to this active principle, the disinfection temperature and/or the active principle dosage, for example. These measurements can be taken by sensors or by any other known means. This disinfection information $I_d$ is transmitted to the data processing unit D (FIG. 2), which determines a degree of disinfection from this information. For example, if the active principle dosage is measured, various degrees of disinfection will be reached when the measured dosage exceeds predetermined dosage thresholds. If UV radiation is used for disinfection, the degree of disinfection can be determined from the length of time the probe is exposed to this radiation, combined with the amount of radiation dispensed into the enclosure.

Thus, at the end of stage A, the system for tracking the use of a probe knows the type, degree, and time of disinfection for the probe whose use is being tracked.

According to the embodiment in which an independent device is provided, such as a device attached to the probe as described above, such a device includes the means for acquiring the identification information $I_i$, the means for acquiring use information regarding the use of said apparatus, and the date and time recording means. The device is able to communicate with an information processing system such as the data processing unit D. Such a device is used to record the identity of the operator performing disinfection, e.g., by means of a badge inserted into a scanning means of the housing, as well as the identity of the probe being disinfected. Once disinfection is finished, the operator enters the information on the degree of disinfection, or the device communicates with the data processing unit D in order to obtain the information on this degree of disinfection.

During a stage B, the probe is stored while waiting to be used. When the probe is placed in a storage enclosure, it is identified and the date is recorded. The storage beginning time is also recorded. When the probe is taken out of the storage enclosure, the storage end time is recorded. This information is transmitted to the processing unit D, as shown by the arrow 2 in FIG. 1.

To this end, the storage enclosure comprises means for acquiring the identity of the probe, which are of the same type as those provided for the disinfection stage. These means can be associated with the storage enclosure or can be part of an independent, portable device located in the storage room. According to an embodiment, the independent device is the same as that used for disinfection, and it accompanies the probe into the storage room. According to an embodiment, provision is made so that the storage enclosure comprises identification means so that the identity of the enclosure used for storing the probe is transmitted to the data processing unit D.

The data processing unit D links the information obtained on disinfection of the probe with the information obtained on its storage. "Linking the information" is taken to mean that the processing unit relates the disinfection information to the storage information using the probe identification information, in such a way that for a probe identity, the processing unit can, for example, compare the degree of disinfection of the probe with its storage time.

Actually, for each type of disinfection and degree of disinfection, there is a corresponding maximum storage time. If the storage time of the probe exceeds the maximum storage time corresponding to the type and the degree of disinfection performed on the probe, then a new disinfection must be performed in order to make sure that the probe can be legitimately used from the standpoint of hygiene.

Thus, when the probe is taken out of the storage enclosure to be used, the data processing unit D verifies that the probe has been disinfected and compares the probe storage time to the maximum storage time corresponding to the disinfection performed on the probe.

If the probe has not been disinfected before being stored, the data processing unit D produces an order prohibiting the use of the probe, and the storage enclosure emits a rejection signal for the probe. The probe is not used, then, and is sent back to the disinfection stage A, as shown by the arrow 3 in FIG. 1.

If the storage time exceeds the maximum storage time, the data processing unit produces an order prohibiting the use of the probe. The probe is not used, then, and is sent back to the disinfection stage A, as shown by the arrow 3 in FIG. 1.

If the storage time is less than the maximum storage time, the probe can be safely used from the standpoint of hygiene. The data processing unit D then produces an order authorizing the use of the probe. The probe can then be used during a use stage C, as shown by the arrow 4 in FIG. 1.

In the stage C in which the probe is used on a patient, the probe is identified and the exam date is recorded. This identification and the date are transmitted to the data processing unit D, as shown by the arrow 5 in FIG. 1. The processing unit links this information, and a sequencing of disinfection and use is done. Thus, for a given probe identity, all the information regarding pre-use actions is known and put in chronological order. This way, one can ascertain that a chain of actions has been properly completed before allowing the probe to be used. The probe identity and legitimacy-of-use verification checks can be performed by the apparatus with which the probe is used, such as an imaging device, or by the independent, portable device already used during disinfection and storage. The imaging device or the independent device comprises a means for reading a physician identification badge.

Thus, if the identified probe has not been disinfected prior to use, the data processing unit D produces an order prohibiting the use of the probe and transmits it to the imaging device or the independent, portable device. The probe is not used, then, and is sent back to the disinfection stage A, as shown by the arrow 6 in FIG. 1.

If an order authorizing the use of the probe is produced and the operator in fact intends to use the probe, he confirms this use. This confirmation is recorded by the probe use tracking system, which makes it possible to ascertain whether a probe has been used or not. A usage confirmation of this kind is crucial, particularly if multiple probes are connected to the same medical imaging device. That is, in this case, multiple probes can be activated without necessarily being used subsequently, and then it becomes impossible to see from the outside whether a probe has in fact been used or not. The probe usage confirmation makes it possible to ascertain which probe was in fact used, and which probes were only activated, but not subsequently used. The usage confirmation makes it possible to ascertain the disinfection needs of a particular probe.

The probe usage tracking system comprises means for entering information regarding the use of the medical device. Thus, the physician who uses the probe on a patient can enter information on the use of the probe in order to provide data to the data processing unit D. For example, the information entered by the physician comprises the identity of the physician, the name of the patient, the type of treatment for which the probe is used, the patient pathology, and/or information on the system (e.g., the type of ultrasonograph) in which the device is used. In practice, this information can also be recovered from the data processing unit D by the imaging device or the independent device.

A record of the length of time the probe is used and information on the environment in which the probe is used can also be provided using means (sensors, etc.) similar to those used for probe disinfection.

The usage confirmation for a probe and all the above-mentioned information are transmitted to the data processing unit D, which links them with the information regarding disinfection and storage, and in this way produces an order authorizing or an order prohibiting the use of the probe based on an analysis using this information to determine whether it is legitimate from the hygienic standpoint to use the probe. In addition, linking all this information creates a waiting list, which is constantly being updated, of the medical apparatuses needing to be disinfected. This waiting list lets the people responsible for disinfection know which apparatuses to disinfect first, and it enables the storage enclosures to reject apparatuses that still appear on this waiting list.

Thus, if the type of treatment for which the probe is used requires a particular degree of disinfection, the processing unit verifies whether the probe was disinfected to the required degree, and if so, authorizes its use, and if not, prohibits its use.

If the environment (temperature, humidity, etc.) in which the probe is used is not an ideal environment for the use of the probe, the processing unit prohibits the use of the probe.

Other authorization and prohibition criteria for the probe may be provided and recorded in the data processing unit D, which produces the authorization or prohibition order for the probe based on these criteria and the information transmitted during the above-mentioned stages. These criteria may be standards established in the medical field, for example, and are recorded in the processing unit D, which verifies whether these criteria have been met prior to authorizing the use of the probe. All of these criteria are combined in order to authorize or prohibit the use of the probe.

To this end, the tracking system is provided with means for storing the information acquired and processed by the acquisition and processing system.

A history tracking the use of the probe is also recorded. This way, after the probe is used by a physician, the data processing unit D can produce specific disinfection instructions (degree and type of disinfection) depending on the type of treatment for which the probe was used, as shown by the arrow 7 in FIG. 1.

Likewise, if the probe has a particular known useful life, the tracking system can determine whether the probe can still be used or whether it must be replaced according to the recorded history.

The invention thus makes it possible to guarantee that a particular probe is always used legitimately from the standpoint of hygiene, and to prevent a dangerous use of this probe.

The invention claimed is:

1. Method for tracking the use of a medical apparatus in order to determine whether said apparatus can be safely used from a hygienic standpoint, wherein said apparatus comprises a probe and an apparatus identifier, wherein the method comprises: disinfecting the probe with a portable disinfection device, and when the apparatus is disinfected, using an information acquisition and processing system to acquire information identifying said apparatus and information regarding the disinfection and use of said apparatus.

2. Tracking method according to claim 1, which additionally comprises a stage in which information regarding the apparatus storage time is recorded by the information acquisition and processing system, wherein said storage information is sequenced in with the disinfection and use information, and the information acquisition and processing system produces a disinfection order if the storage time exceeds a predetermined threshold and an order prohibiting the use of the apparatus if it is not disinfected.

3. Method according to claim 1, wherein recording the disinfection information about the type and degree of disinfection includes recording the active principle used for disinfection, the length of time the apparatus was exposed to this active principle, the disinfection temperature and/or the active principle dosage.

4. Method according to claim 3, wherein the information acquisition and processing system produces a notice of adequate or inadequate disinfection based on the disinfection information about the type and degree of disinfection.

5. Method according to claim 4, wherein if a notice of inadequate disinfection is produced, the system prohibits the use of the apparatus.

6. Method according to claim 1, wherein, while the apparatus is being disinfected, the identity of the operator performing the disinfection is recorded.

7. Method according to claim 1, wherein recording the use information regarding the type of use of the apparatus includes recording the identity of the attending physician, the identity of the patient, the type of treatment for which the apparatus is used, the type of pathology of the patient, the length of time the apparatus is used, the information on the environment in which the apparatus is used and/or the information on the system in which the apparatus is used.

8. Method according to claim 1, wherein the information acquisition and processing system records a history tracking the use of the medical apparatus and the legitimacy of its use.

9. System for tracking the use of a medical apparatus that makes it possible to implement the method according to claim 1, wherein said system comprises, an information acquisition and processing system that acquires information identifying said apparatus, acquires use information regarding the use of said apparatus, records the date and time, and associates identification and use information for said apparatus with date and time information.

10. Tracking system according to claim 9, wherein the information acquisition and processing system is contained in a portable device.

11. Tracking system according to claim 10, wherein the portable device comprises a sensor, and the sensor measures the degree of disinfection of the medical apparatus.

12. Tracking system according to claim 9, wherein the identifier associated with the medical apparatus comprises a RFID chip permanently fixed on said apparatus.

13. Tracking system according to claim 9, wherein the identity acquisition component comprises a RFID chip scanner.

14. Method according to claim 1, wherein said acquisition and processing system further records the date of disinfection.

15. Method according to claim 1, wherein said acquisition and processing system further records information about the type and degree of disinfection.

16. Method according to claim 1, wherein said acquisition and processing system further records information about the type of use of said apparatus on a patient.

17. Method according to claim 16, wherein said acquisition and processing system further sequences the disinfection information and the information about use on the patient.

18. Method according to claim 17, wherein prior to each use, said acquisition and processing system produces an order authorizing or prohibiting the use of said apparatus based on the sequencing, with its use being authorized if, following a particular use, an appropriate disinfection process for this use has taken place.

* * * * *